United States Patent [19]

Freeman et al.

[11] Patent Number: 5,084,016
[45] Date of Patent: Jan. 28, 1992

[54] EPIDURAL CATHETER APPARATUS WITH AN INFLATION FITTING

[76] Inventors: Andrew B. Freeman, 5525 Willow La., Dallas, Tex. 75230; H. A. Tillmann Hein, 4346 Meadowdale La., Dallas, Tex. 75229

[21] Appl. No.: 602,165

[22] Filed: Oct. 23, 1990

Related U.S. Application Data

[62] Division of Ser. No. 403,107, Sep. 5, 1989, Pat. No. 5,024,655.

[51] Int. Cl.$^5$ .............................................. A61M 25/00
[52] U.S. Cl. ...................................................... 604/103
[58] Field of Search ............................ 128/656-658; 606/108, 192-196; 604/43, 96-103, 167, 256, 264, 280, 283

[56] References Cited

U.S. PATENT DOCUMENTS

| Re. 31,855 | 3/1985 | Osborne | 604/161 |
|---|---|---|---|
| 1,596,754 | 8/1926 | Moschelle | 604/282 |
| 1,928,992 | 10/1933 | Clark et al. | 137/90 |
| 3,044,468 | 7/1962 | Birtwell | 128/349 |
| 3,053,257 | 9/1962 | Birtwell | 128/349 |
| 3,482,576 | 12/1969 | Ericson et al. | 128/349 |
| 3,602,228 | 8/1971 | Cowley | 128/349 |
| 3,677,244 | 7/1972 | Hassinger | 128/214.4 |
| 3,746,003 | 7/1973 | Blake et al. | 128/349 B |
| 3,818,903 | 6/1974 | Bleecker | 128/349 |
| 3,833,003 | 9/1974 | Faricco | 128/347 |
| 4,154,244 | 5/1979 | Becker et al. | 128/349 B |
| 4,207,899 | 6/1980 | Patel | 128/349 B |
| 4,240,433 | 12/1980 | Bordow | 128/347 |
| 4,259,960 | 4/1981 | Taylor | 128/349 |
| 4,526,175 | 7/1985 | Chin et al. | 128/344 |
| 4,531,943 | 7/1985 | Van Fassel et al. | 604/280 |
| 4,583,974 | 4/1986 | Kokernak | 604/99 |
| 4,701,162 | 10/1987 | Rosenberg | 604/103 |
| 4,737,146 | 4/1988 | Amaki et al. | 604/51 |
| 4,787,399 | 11/1988 | Bonello et al. | 128/772 |
| 4,796,615 | 1/1989 | Bullock et al. | 128/202.27 |
| 4,832,692 | 5/1989 | Box et al. | 604/99 |

Primary Examiner—John D. Yasko
Assistant Examiner—Anthony Gutowski
Attorney, Agent, or Firm—Johnson & Gibbs

[57] ABSTRACT

A dual lumen catheter member having distal and proximal end portions is configured to be longitudinally passed entirely through a hollow needle member insertable into the epidural space of a patient, and is provided on its distal end with an inflatable balloon element. With the needle member inserted, the distal catheter end is passed therethrough into the epidural space. The needle member is then withdrawn and removed from the catheter member past its proximal end. The proximal end of the catheter member is then removably inserted into an inlet fitting and frictionally locked therein. The installed inlet fitting defines sealingly separated outward extensions of the lumen inlets which are spaced longitudinally apart on the proximal catheter end portion. Pressurized fluid is injected into one of these inlet extensions to inflate the balloon element, and an anesthetic fluid is flowed into the other extension, and through its associated lumen, into the epidural space through the distal catheter end therein. The inflated balloon element prevents dislodgement of the distal catheter end from the epidural space and also inhibits its migration therein into, for example, adjacent blood vessels, the subarachnoid space, or out a nerve root sleeve. In an alternate embodiment of the catheter member, the balloon lumen is filled with a pressurized fluid and opens outwardly through the catheter into a second balloon element proximally spaced from the distal tip balloon. Under normal conditions, this pressurized fluid holds the second balloon in an inflated condition while the distal tip balloon is deflated. After the inserted needle is removed past the second balloon member a clip member is forced over the second balloon to compress it and maintain the distal tip balloon in an inflated condition within the epidural space.

1 Claim, 4 Drawing Sheets

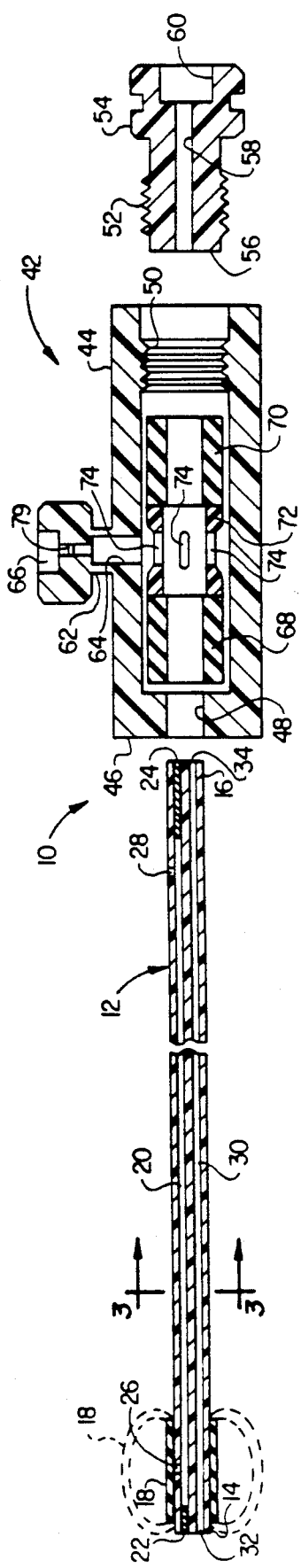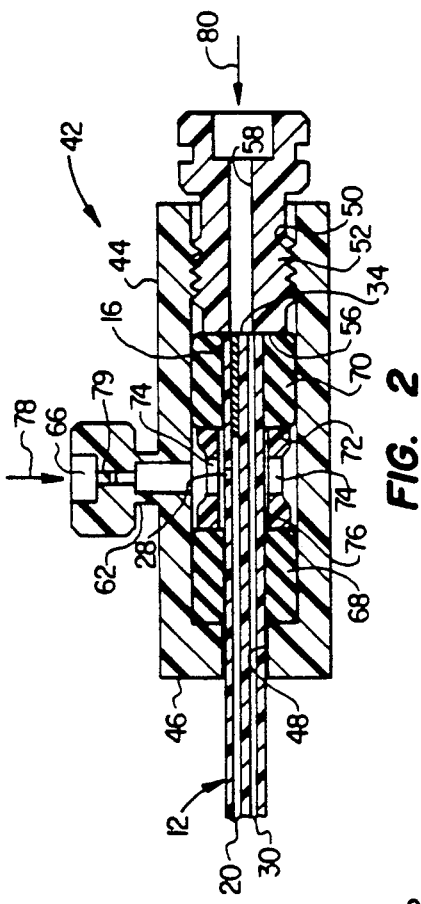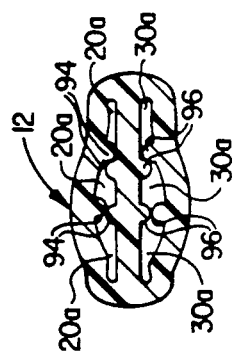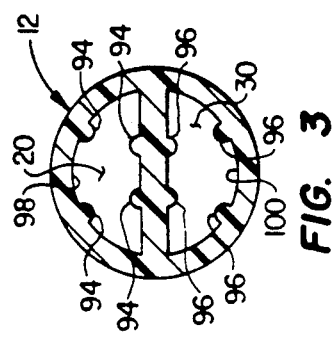
FIG. 1
FIG. 2
FIG. 3A
FIG. 3

EPIDURAL CATHETER APPARATUS WITH AN INFLATION FITTING

This application is a division, of application Ser. No. 403,107, filed Sept. 5, 1989, now U.S. Pat. No. 5,024,655.

BACKGROUND OF THE INVENTION

The present invention relates generally to medical devices and, in preferred embodiments thereof, more particularly provides improved catheter apparatus, and associated methods, for flowing an anesthetic or other fluid into the epidural space of a patient.

Anesthetizing the spinal nerves is conventionally effected by inserting a small diameter hollow needle member into the epidural space (through, for example, a selected interspinous ligament) and then passing the distal end of a smaller diameter catheter member inwardly through the inserted needle into the epidural space. The typical epidural needle is configured at its tip in a manner such that the distal catheter end exits the needle tip in a direction generally transverse to the length of the needle.

To facilitate retention of the distal catheter end within the epidural space after the needle is withdrawn, it is common practice to insert the distal catheter end portion a considerable distance into the epidural space. After catheter insertion therethrough, the needle is withdrawn and an anesthetic fluid is flowed through a lumen within the catheter and outwardly through the distal catheter end within the epidural space. An example of this conventional procedure, using a dual lumen epidural catheter, is illustrated and described in U.S. Pat. No. 4,737,146 to Amaki et al.

While this general procedure is widely used and accepted, it is not entirely free from problems, limitations and disadvantages. For example, the need to insert the distal catheter end a considerable distance into the epidural space raises the possibility of the inserted catheter portion undesirably "migrating" into an adjacent blood vessel, the subarachnoid space, or out a nerve root sleeve, instead of remaining wholly in the epidural space as intended. Additionally, it is often somewhat difficult to precisely control the actual placement of the fluid lumen outlet within the epidural space since the inserted distal catheter end portion (which, of course, is not visible to the person inserting it) can be deflected within the epidural space and come to rest at an unintended location therein, such as a nerve root sleeve.

Further, despite the offsetting of the distal catheter end from its insertion point, the catheter may be quite easily dislodged and pulled out of the epidural space by, for example, patient movement, or the catheter being bumped by another object. Also, in those instances when two epidural catheters are present simultaneously at different spinal levels within a patient's epidural space, the advancement of the catheters to prevent their slipping out can result in their tangling, thereby creating problems in their removal. In an attempt to alleviate this dislodgement problem it is common practice to tape the catheter to the skin at its entry point, or to "tunnel" an adjacent portion of the catheter under the patient's skin. Neither solution to this catheter dislodgement problem has proven to be entirely satisfactory, as neither involves direct fixation of the distal catheter tip.

Another catheter-related problem presented in applications utilizing an insertion needle is that the typical dual lumen catheter element is provided at its proximal or fluid inlet end with a fixed inlet structure (for example, of a "Y" configuration) which is considerably larger, in a lateral cross-sectional sense, than the balance of the elongated catheter element. This conventional proximal catheter end configuration, in an epidural catheter, is illustrated in the aforementioned U.S. Pat. No. 4,737,146 to Amaki et al. Examples of this laterally enlarged "Y" configuration at the proximal end of a non-epidural catheter are representatively illustrated in U.S. Pat. No. 3,482,576 to Ericson et al; U.S. Pat. No. 3,818,903 to Bleecker; U.S. Pat. No. 4,154,244 to Becker et al; U.S. Pat. No. 4,207,899 to Patel; and U.S. Pat. No. 4,259,960 to Taylor.

The laterally enlarged inlet configuration on the proximal end of conventional dual lumen catheter elements captively retains the epidural insertion needle on the catheter element after the distal end of the catheter has been inserted into the epidural space and the needle has been subsequently withdrawn from the patient's body. This adds undesirable bulk to the overall catheter structure, which must often be left in place for considerable periods of time. Additionally, the withdrawn needle has a tendency to slide back and forth along the outwardly projecting catheter element portion and must usually be taped or otherwise secured to the catheter to prevent this awkward and undesirable shifting of the withdrawn needle along the length of the catheter element, and possible cutting of the catheter by the sharp end of the needle. In addition, the exposed needle point is a hazard both to the patient and to the attending medical personnel.

Like conventional catheters used in other applications, conventional epidural catheter elements also have a tendency to undesirably shut off fluid flow therethrough when sharply bent or kinked due to the heretofore unavoidable pinching shut of their internal fluid flow lumens. Accordingly, considerable care must be taken to assure that the installed catheter is kept free from sharp bends and kinks. This is often a somewhat difficult task, particularly when a long catheter is used and left in place for extended periods of time without professional supervision. Shifting of the patient's body can easily pinch off the catheter lumen or lumens. The catheter may also be kinked by the combination of outward migration of the non-fixed distal catheter tip portion and the fixation of the catheter at the skin or other non-distal location creating redundant catheter length.

In view of the foregoing it can readily be seen that a need exists for various improvements in epidural catheter apparatus and associated methods of flowing anesthetic or other fluids into the epidural space. It is accordingly an object of the present invention to provide such improvements.

SUMMARY OF THE INVENTION

In carrying out principles of the present invention, in accordance with a preferred embodiment thereof, improved epidural catheter apparatus is provided which comprises an elongated flexible catheter element having a proximal end portion, a distal end portion, and an inflatable retention balloon element secured to and laterally circumscribing the distal end portion.

An inflation lumen extends longitudinally through the catheter element and has a laterally extending outlet communicating with the interior of the balloon, and an inlet opening outwardly through the proximal end portion of the catheter element. A fluid injection lumen also extends longitudinally through the catheter element, and has an outlet extending longitudinally outwardly through the distal catheter end and an inlet extending longitudinally outwardly through the proximal catheter end. With the distal end retention balloon in its normal deflated condition, the catheter is laterally configured in a manner such that it may be longitudinally passed entirely through a small diameter hollow insertion needle member conventionally used in epidural anesthetic procedures.

The epidural catheter apparatus also includes a specially designed inlet fitting into which the proximal end portion of the catheter may be inserted. Tightening of a cap member portion of the inlet fitting deforms resilient compression members around the inserted catheter member portion to frictionally lock it within the inlet fitting. The deformed compression members also sealingly separate the two lumen inlets which communicate with outward extensions thereof formed within and opening outwardly through the inlet fitting body.

To use the catheter apparatus, an insertion needle member is inserted through a selected interspinous ligament into the epidural space, and the distal end portion of the catheter is passed inwardly through the inserted needle to position the deflated retention balloon within the epidural space. The needle is then withdrawn, pulled off the catheter past its proximal end, and discarded. The inlet fitting is then operatively attached and frictionally locked to the proximal catheter end portion, and a suitable pressurized fluid is injected into one of the spaced apart inlet fitting inlets to inflate the retention balloon within the epidural space. Finally, an anesthetic fluid is forced into the other inlet fitting body inlet to flow the fluid into the epidural space.

The inflated balloon serves to retain the catheter within the epidural space, and at the same time inhibits undesired migration of the distal catheter end within the epidural space—for example into an adjacent blood vessel or into the subarachnoid space, or out a nerve root sleeve.

According to a feature of the present invention, the interior surfaces of the catheter lumens have formed thereon circumferentially spaced series of longitudinally extending, inwardly projecting ribs which function to prevent complete closure of the lumens at a location of the catheter which is sharply bent or kinked.

In alternate embodiments of the catheter apparatus, a screw-on plunger cap is connectable to one of the inlet fitting inlets and is usable to inflate the retention balloon, and a resilient locking member is positioned within the inlet fitting body and is deformable into a groove formed in the proximal catheter end to even more firmly hold the catheter within the installed inlet fitting.

In a further alternate embodiment of the catheter apparatus, the laterally extending inlet of the inflation lumen is moved distally away from the proximal end portion of the catheter, and a second balloon element is secured over this repositioned lumen inlet. The inflation lumen is filled with a pressurized fluid which serves to normally hold the second balloon in an inflated condition while permitting the distal end balloon to normally remain in a fully deflated condition.

When the inserted needle member is removed from the catheter member it passes over and temporarily compresses the second balloon. A specially designed annular clamp member is then threaded onto the catheter member. The installed clamp member is then forced over the re-inflated second balloon member to compress it and inflate the distal retention balloon element within the epidural space.

BRIEF DESCRIPTION OF THE DRAWINGS

FIG. 1 is an enlarged scale, longitudinally foreshortened and partially exploded cross-sectional view through an epidural catheter apparatus embodying principles of the present invention, the illustrated apparatus including a dual lumen catheter element and an inlet fitting removably connectable to the proximal end of the catheter element;

FIG. 2 is a cross-sectional view through a proximal end portion of the catheter element with the inlet fitting operatively connected thereto;

FIG. 3 is an enlarged scale cross-sectional view through the catheter element, taken along line 3—3 of FIG. 1, and illustrates flow stoppage prevention projections formed therein;

FIG. 3A is a cross-sectional view similar to that in FIG. 3 and illustrates the operation of the interior catheter projections when the catheter element is sharply bent;

DETAILED DESCRIPTION

Figure 4:
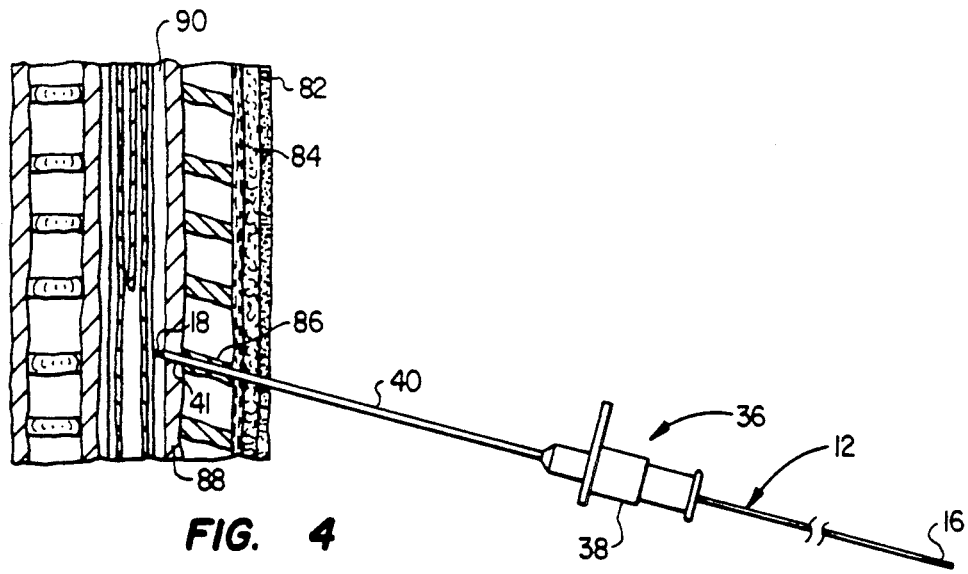
FIGS. 4, 4A, 4B are simplified, somewhat schematic elevational and longitudinally foreshortened views of the catheter apparatus sequentially illustrating its use in conjunction with the cross-sectionally illustrated epidural space of a patient.

Cross-sectionally illustrated in FIG. 1 is an improved epidural catheter apparatus 10 which embodies principle of the present invention and includes an elongated flexible catheter member 12 which, for purposes of scale and illustrative clarity, has been substantially foreshortened. Catheter member 12 has a left or distal end portion 14 and a right or proximal end portion 16. An inflatable retention balloon element 18 is suitably secured to and laterally circumscribes the distal end portion 14, the balloon 18 normally being in a deflated condition (indicated by its solid line position in FIG. 1), but being inflatable to its dotted line position in a manner subsequently described.

Extending longitudinally through the catheter member 12 is an inflation lumen 20 which is blocked at its distal and proximal ends by suitable plug members 22 and 24. Lumen 20 is provided with an outlet opening 26 which extends laterally outwardly through the catheter element 12 into the interior of the balloon 18, and an inlet opening 28 which extends laterally outwardly through the catheter member inwardly of the proximal end plug 24. Also extending longitudinally through the catheter member 12 is a fluid injection lumen 30 having an outlet 32 on the distal catheter end, and an inlet opening 34 positioned on the proximal catheter end and spaced rightwardly from the inlet opening 28.

In a manner subsequently described, the catheter member 12 may be utilized in conjunction with a conventional needle 36 (FIG. 4) comprising a hollow hub 38 from which an elongated hollow needle member 40 outwardly extends, the needle member being of a very small diameter suitable for epidural anesthesia applications. For an important purpose later described, it is important to note at this point that the catheter member 12 is laterally configured along its entire length in a manner permitting it, when the balloon 18 is in its deflated orientation, to be longitudinally passed entirely through the hollow needle member 40. More specifically, it should be noted that the proximal end portion 16 of the dual lumen catheter member 12 is of the same lateral dimension as the balance of the catheter member—it is not provided with a laterally enlarged inlet end configuration as typically incorporated in conventional dual lumen catheters.

Referring again to FIG. 1, the epidural catheter apparatus 10 also includes a unique dual flow path inlet fitting 42 which may be removably secured to the proximal catheter member end portion 16 in a manner subsequently described. Inlet fitting 42 includes a hollow tubular plastic body 44 having a left end wall 46 with a central circular opening 48 formed therein and sized to slidably receive the proximal end portion 16 of the catheter member 12. The right end of the body 44 has an internally threaded opening 50 adapted to receive the externally threaded, reduced diameter end portion 52 of a cap member 54. The cap end portion 52 has a left end 56 through which a circular opening 58 rightwardly extends, the opening 58 having a radially enlarged portion 60 which extends through the right end of the cap member, as in a conventional Luer fitting. Extending laterally outwardly from a longitudinally intermediate section of the inlet fitting body 44 is a hollow conduit portion 62 which communicates with interior of the body 44 via an opening 64 formed in its side wall. As illustrated, the outer end of the conduit 62 is enlarged and provided with a counterbored inlet opening 66, as in a conventional Luer fitting. The counterbored conduit inlet opening 66 and the counterbored cap member opening 58, 60 are configured to receive the ends of conventional syringes (not illustrated) used to inject pressurized fluids into these openings for purposes later described.

Coaxially disposed within the interior of the inlet fitting body 44 are a pair of hollow tubular rubber compression members 68 and 70 which are adapted, in their uncompressed states (FIG. 1), to coaxially and slidably receive the proximal end portion 16 of the catheter member 12. The compression members 68 and 70 are spaced apart within the body 44 by a hollow cylindrical rigid plastic spacing member 72 whose interior diameter is slightly larger than the interior diameters of the compression members 68 and 70. A longitudinally central portion of the spacing member 72 is laterally inset and has formed therethrough a circumferentally spaced series of axially elongated openings 74.

To rapidly install the inlet fitting 42 on the proximal end portion 16 of the catheter member 12, the cap portion 52 is threaded into the inlet fitting body opening 50 until the cap end 56 engages the right compression member 70 and drives the left compression member 68 into engagement with the interior surface of the body endwall 46. The proximal catheter member end portion 16 is then rightwardly inserted sequentially through the body opening 48, the interior of the compression member 68, the interior of the spacing member 72, and into the interior of the compression member 70. The cap member 54 is then further tightened, as indicated in FIG. 2, to axially compress the compression members 68 and 70. This axial compression of the members 68 and 70 also radially deforms them in both inward and outward directions. In turn, this radial deformation frictionally locks the compression members 68, 60 against the interior side surface of inlet fitting body 44, and also frictionally locks the catheter to the interior side surfaces of the deformed compression members. The amount of this frictional locking may be selectively increased by tightening the cap 54, or decreased by loosening the cap 54.

In this frictionally locked position of the proximal end portion of the catheter member, the inlet opening 28 of the inflation lumen 20 is generally longitudinally aligned with the spacing member openings 74 and with the body side wall opening 64. As illustrated in FIG. 2, the lumen inlet opening 28 is surrounded by a small annular space 76 defined by the interior side surface of the spacing member 72. With the proximal catheter end portion 16 frictionally locked within the inlet fitting body 44 in this manner, the conduit 62, the spacing member side opening 74 and the annular space 76 define an outward extension of the inflation lumen inlet opening 28, and the cap member opening 58, 60 forms an outward extension of the fluid injection lumen inlet 34.

Importantly, the deformed compression member 70 sealingly separates the lumen inlets 28 and 34 (and their outward extensions) from one another within the interior of the inlet fitting body 44. Additionally, the deformed compression member 68 sealingly separates the lumen inlet 28 from the body end wall opening 48. Accordingly, by inserting a suitable syringe (not shown) into the counterbored conduit opening 66, compressed fluid 78 can be forced sequentially through the conduit 62, the body side wall opening 64, the spacing member side openings 74, the annular space 76, and the lumen inlet opening 28, into the lumen 20 to inflate the retention balloon element 18 as illustrated in dotted lines in FIG. 1. To prevent escape of the fluid 78 from the inlet fitting 42 after the balloon inflation syringe has been removed from opening 66, a schematically depicted check valve element 79 may be operatively installed in an inner end portion of opening 66 as indicated. In a similar fashion a fluid injection syringe (not shown) can be inserted into the cap opening 58, 60 to force an anesthetic fluid 80 into the lumen 30, through its inlet opening 34, for outflow through the outlet opening 32 of the fluid injection lumen 30.

As used herein, the term "fluid" is intended to encompass any flowable material such as a gas, a liquid, a slurry or suspension such as a gas/solid mixture or a liquid/solid mixture, a solution or the like. Thus, for example, the balloon pressurization fluid 78 could be a liquid or a gas, and the fluid 80 ultimately flowed into the epidural space through the lumen 30 is not limited to a liquid or a gas. Additionally, while the fluid 80 is representatively an anesthetic fluid, it will be appreciated that other types of fluids, such as analgesic solutions, could alternatively be flowed into the epidural space through the catheter lumen 30.

Figure 4A:
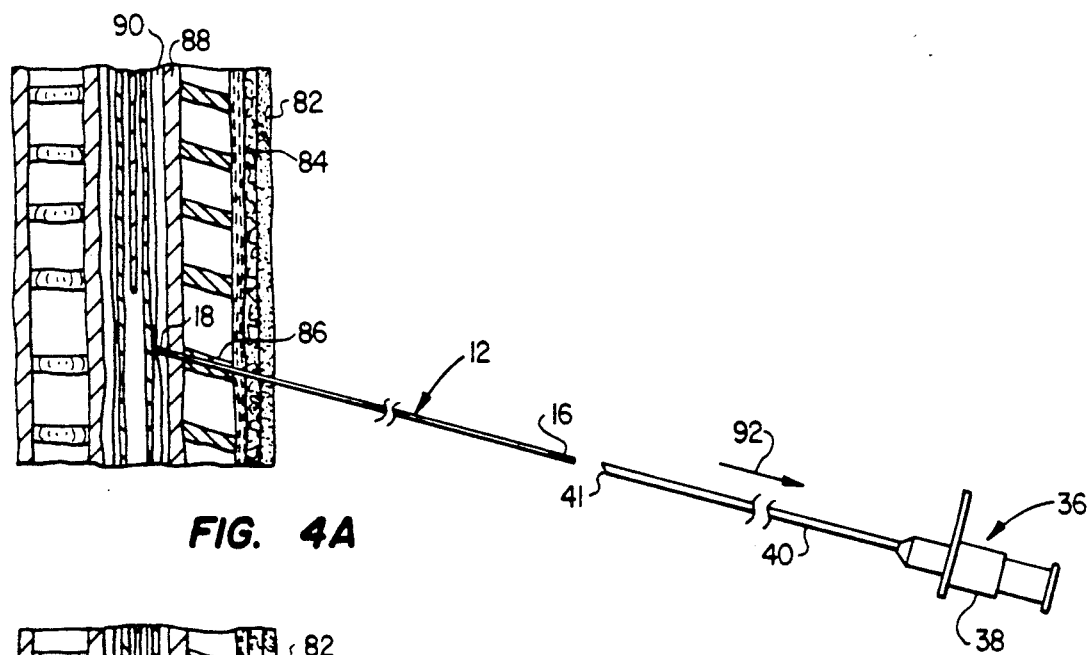
Figure 4B:
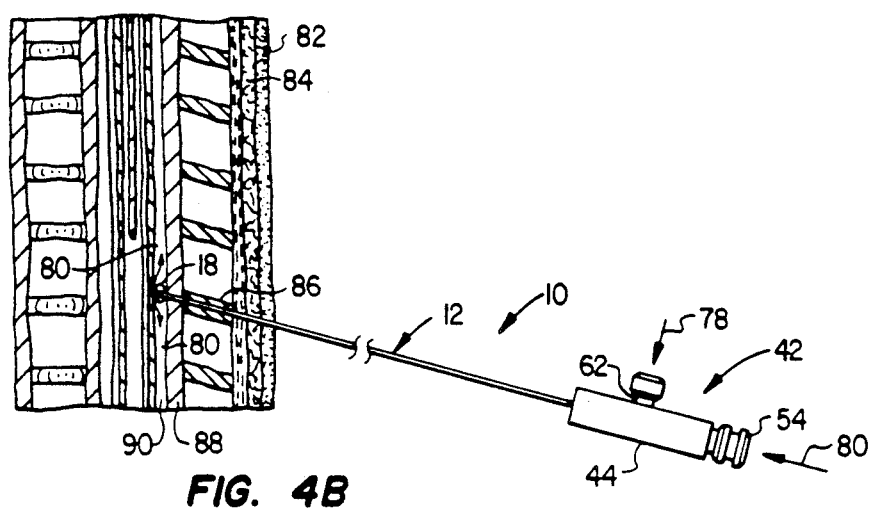

Referring now to FIGS. 4, 4A and 4B, the use of the improved epidural catheter apparatus 10 will be described in detail. As illustrated in FIG. 4, the first step, performed in a conventional manner, entails the insertion of the sharpened end 41 of the needle member 40 sequentially through the skin 82 of the patient, the subcutaneous tissue 84, a selected interspinous ligament 86, and the ligamentum flavum 88 into the epidural space 90. Next, the balloon-tipped distal end portion of the catheter element 12 is longitudinally passed through the needle hub 38 and the hollow needle member 40 until retention balloon 18 enters the epidural space 90 as depicted in FIG. 4.

With the deflated balloon 18 positioned within the epidural space 90 as shown in FIG. 4A, the needle 36 is simply pulled off the catheter member 12 as indicated by the arrow 92, past its proximal end portion 16. The needle 36 can then be simply discarded.

Finally, as depicted in FIG. 4B, the inlet fitting 42 is positioned on and frictionally locked to the proximal catheter member end portion 16, as previously described, by tightening the cap member 54. Pressurized fluid 78 may then be flowed into the inlet fitting conduit portion 62 to inflate the retention balloon 18 within the epidural space 90, and anesthetic fluid 80 may be flowed inwardly through the cap member 54 and forced leftwardly through the fluid injection lumen 30 for discharge through its outlet opening 32 into the epidural space 90.

A variety of advantages presented by the improved epidural catheter apparatus 10 may be readily discerned in FIG. 4B. For example, there is no insertion needle left on the catheter member 12 to slide around thereon—the previously utilized needle 36, as just described, has been totally removed from the catheter member and discarded. There is accordingly no need to tape or otherwise restrain the insertion needle on the catheter member, and its needle member point is no longer in a position to potentionally jab either the patient or the operator of the catheter structure, or to cut the catheter. The absence of the insertion needle on the in-place catheter structure also considerably lightens it.

The inflated retention balloon 18 within the epidural space 90 provides a very advantageous dual function therein. First, it essentially prevents the accidental dislodgement and withdrawal of the catheter member 12 from the epidural space, the inflated balloon being considerably larger than the patient insertion opening through which it was originally passed, as can be seen in FIG. 4B.

Additionally, the inflated retention balloon 18 substantially inhibits undesirable "migration" of the distal catheter end within the epidural space into an adjacent blood vessel, the subarachnoid space, or out a nerve root sleeve. This antimigration feature of the improved catheter structure of the present invention is further enhanced because it is not necessary (due to the use of the retention balloon 18) to pass the distal catheter end as far into and along the epidural space 90 as is customary under conventional practice. All that is necessary is to insert the distal catheter end into the epidural space a distance sufficent to completely place the balloon 18 therein, and to prevent accidental removal of the catheter tip from the epidural space during removal of the needle from the patient and the catheter. Moreover, since lengthy insertion distances are not required using the catheter apparatus 10, the actual outflow of the anesthetic fluid 80 into the epidural space may be very precisely positioned. Simply stated, such fluid outflow into the epidural region occurs closely adjacent the juncture of the ligamentum flavum 88 and the interspinous ligament 86 through which the needle member was originally inserted.

Another problem commonly encountered in catheter elements, of either the single or multi-lumen types, in their tendency to shut off fluid flow at locations at which they are sharply bent or "kinked". More specifically, when the typical catheter element is sharply bent, each of its internal lumens is typically crimped shut. According to another feature of the present invention, illustrated in FIG. 3, this well-known problem is essentially eliminated by the provision of circumferentially spaced series of longitudinally extending, inwardly projecting ribs 94 and 96 respectively formed along the interior side surfaces 98 and 100 of the catheter lumens 20 and 30. As illustrated in FIG. 3A, in the event that the catheter member 12 is sharply bent, or "kinked", at a given location thereon, the ribs 94 and 96 are brought to bear against generally opposite interior side surface portions of their associated lumen to maintain at the sharply bent location at least minimal open portions 20a and 30a of the lumens 20 and 30.

Figure 5:
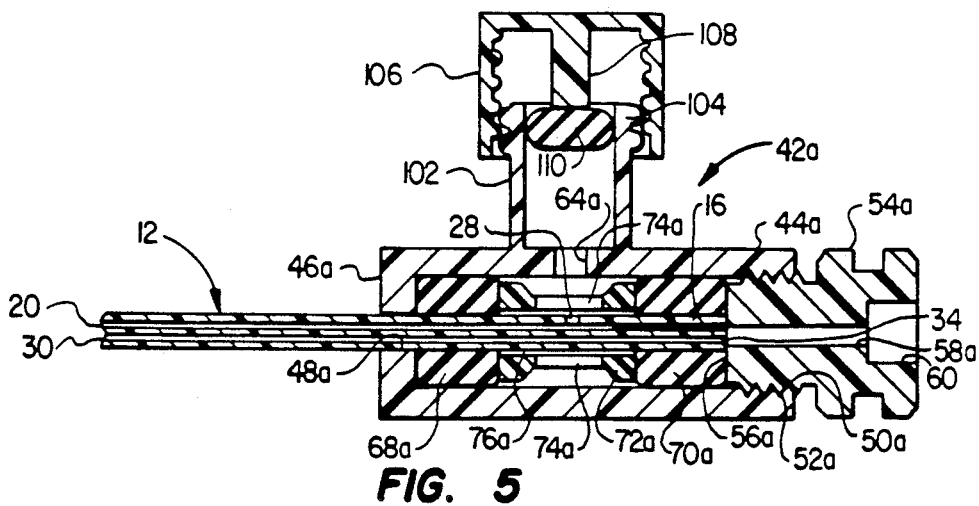
FIG. 5 is a cross-sectional view through a proximal end portion of the catheter element with a first alternate embodiment of the inlet fitting operatively secured thereto.

An alternate embodiment 42a of the previously described inlet fitting 42 is cross-sectionally illustrated in FIG. 5 and is shown operatively connected to the proximal end portion 16 of the catheter member 12. Except for the omission from the inlet fitting 42a of the inlet conduit 62 (FIG. 1), it is substantially identical to the previously described inlet fitting 42. For ease in comparison, the components in the inlet fitting 42a similiar to those in inlet fitting 42 have been given identical reference numerals having the subscripts "a".

In place of the inlet conduit 62, the inlet fitting 42a is provided with an inlet conduit 102 which circumscribes the body side opening 64a and has an open, externally threaded outer end 104. To inflate the retention balloon 18, an internally threaded cap member 106 is threaded onto the conduit end portion 104. Cap member 106 internally carries an axially extending post portion 108 at the lower end of which a resilient seal member 110 is secured. As the cap 106 is threaded onto the conduit 102, the resilient number 110 sealingly engages the interior side surface of the conduit 102 and is forced downwardly therethrough. The downward movement of the seal member 110 within the conduit 102 compresses the air within the interior of the conduit 102 and correspondingly elevates the pressure within the inflation lumen 20 until the retention balloon 18 is inflated. The use of this cap member/plunger seal construction, by appropriate sizing thereof, permits very precise control of retention balloon inflation size, and prevents overinflation and bursting of the balloon 18.

Figure 6:
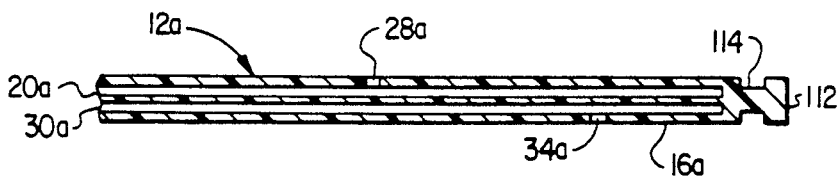
FIG. 6 is a cross-sectional view through a modified proximal end portion of the catheter element.
Figure 7:
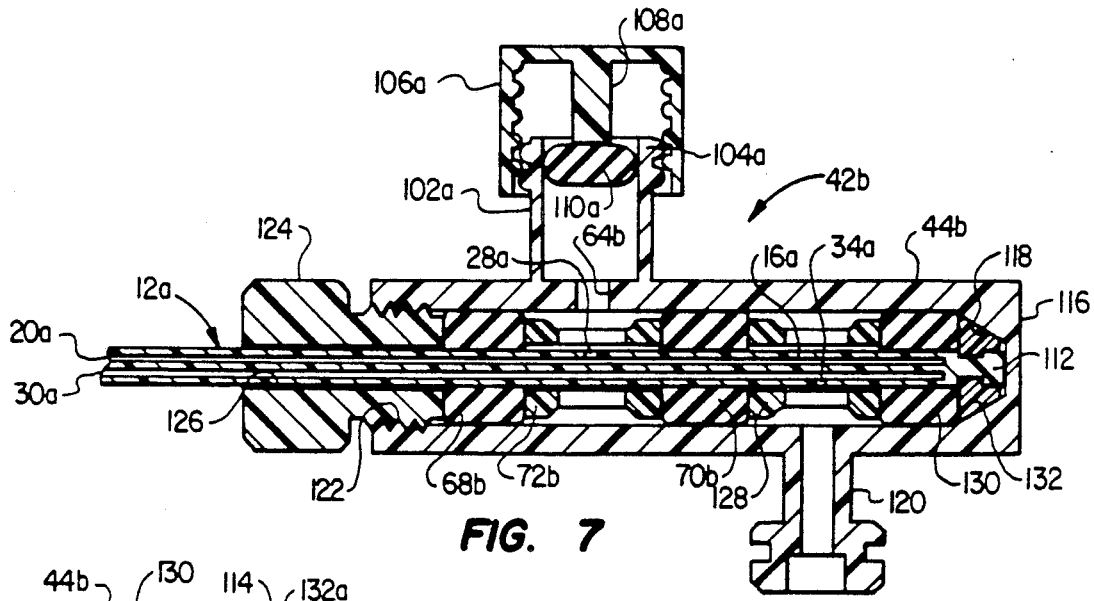
FIG. 7 cross-sectionally illustrates a second alternate embodiment of the inlet fitting operatively connected to the proximal catheter element end portion shown in FIG. 6.

A proximal end portion 16a of an alternate embodiment 12a of the previously described catheter member 12 is cross-sectionally illustrated in FIG. 6, and is shown operatively connected to a second alternate embodiment 42b of the inlet fitting 42 in FIG. 7. For ease in comparison, the elements in catheter member 12a similar to those in catheter member 12 have been given identical reference numerals having the subscript "a", and the components in the inlet fitting 42b similiar to those in the inlet fitting 42 have been given identical reference numberals with the subscript "b".

As illustrated in FIG. 6, the proximal ends of the catheter lumens 20a and 30a terminate within the body of the catheter member 12a inwardly adjacent its proximal end 112. The inlet opening 34a of the fluid injection lumen 30a does not pass longitudinally outwardly through the proximal end of the catheter member. Instead, it passes laterally outwardly through the catheter member side wall at a position longitudinally spaced apart from the lumen inlet opening 28a toward the proximal end 112. As illustrated, and for a purpose later described, the proximal end 112 of the catheter member 12a has formed thereon an annular notch 114.

The inlet fitting body 44b (FIG. 7) has a closed right end 116 having a conically tapered interior surface 118, an inlet extension 120 communicating with the interior of the fitting body and positioned between the side wall opening 64b and the closed right end 116, and an open, internally threaded left end 122 adapted to threadingly receive a cap member 124 having a central opening 126 extending axially therethrough. An inlet conduit 102a (similar to the inlet conduit 102 in FIG. 5) circumscribes the side wall opening 64b and has an open, externally threaded outer end 104a to which a cap member 106a, similar to the cap member 106 in FIG. 5 and having an internal seal member 110a, may be threadingly secured.

Figure 7A:
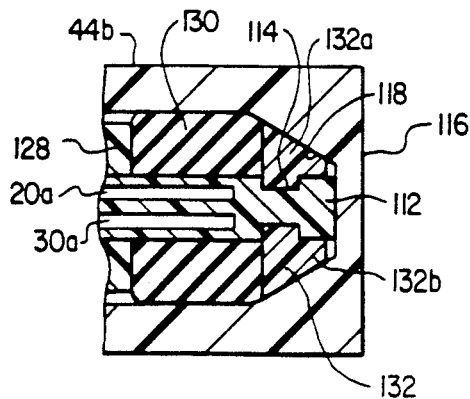
FIG. 7A is an enlargement of a right end portion of FIG. 7.

To secure the proximal end portion 16a of the catheter member 12a within the inlet fitting 42b, the proximal catheter member end portion 16a is sequentially passed rightwardly through the cap member opening 126, the compression member 68b, the spacing member 72b, the compression member 70b, an additional rigid spacing member 128, an additional compression member 130, and into the interior of a locking member 132 disposed within the interior of the inlet fitting body 44b against the conically tapered interior wall surface 118 (see FIG. 7A).

Figure 8:
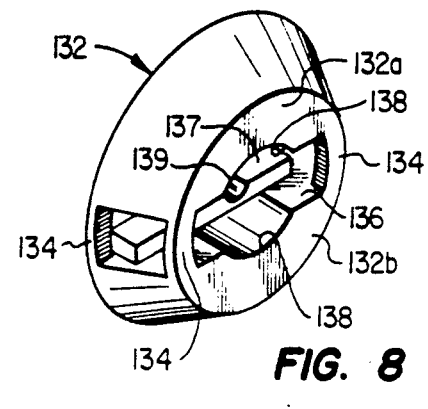
FIG. 8 is an enlarged scale perspective view of a catheter end lock fitting illustrated in FIG. 7A.

As best illustrated in FIGS. 7A and 8, the locking member 132 has a hollow, generally frustroconical configuration defined by spaced apart lateral portions 132a and 132b which are resiliently interconnected by four relatively thin arm portions 134. The lateral portions 132a, 132b have facing interior side surfaces with front portions 136 and raised rear portions 137. Arcuate notches 138, 139 are respectively formed in these side surface portions 136, 137. Each of the notches 138 has a radius substantially identical to that of the proximal catheter end portion 112, and each of the notches 139 has a radius substantially identical to the radius of the annular catheter notch 114. Additionally, the axial widths of the locking member interior side surface portions 137 are slightly smaller than the axial width of the catheter notch 114. The proximal end 112 of the catheter member 12a is slidingly advanced rightwardly through the locking member 132.

After the catheter 12a is passed until it contacts the right end 116 of the inlet fitting 42b, the cap member 124 is tightened into the internally threaded inlet fitting body opening 122 to axially compress each of the three compression members 68b, 70b and 130 as illustrated. As previously described, this axial compression of the compression members also radially compresses them against the interior side surface of the body 44b and the exterior side surface of the catheter member 12a to frictionally lock the proximal catheter member end portion 16a within the inlet fitting 42b. This frictional locking of the catheter member within the inlet fitting 42b is augmented by a positive interlock between the proximal catheter end 112 and the locking member 132 which is achieved as rightward sliding of the locking member 132 against the conical interior surface 118 of the inlet fitting body 44b compresses the resilient locking member arms 134 such that portions 132a and 132b approach each other and the leftward inner notch portions 139 enter the annular notch 114 of catheter 12a, and the rightward notch portions 138 are brought to bear against the side surface of the proximal end 112 of catheter 12a. As illustrated in FIG. 7A, this causes a left end portion of the locking member 132 to enter the catheter notch 114, thereby anchoring the catheter to the locking member. Even if the frictional grip of the three compression members on the proximal catheter end portion 16a becomes loosened, the locking member 132 will substantially prevent the catheter from being withdrawn from the interior of the assembled inlet fitting 42b.

The three deformed compression members 68b, 70b and 130 sealingly separate the lumen inlets 28a and 34a so that fluid flow into lumen 20a is separated from fluid inflow to lumen 30a via the inlet extension 120.

Figure 9:
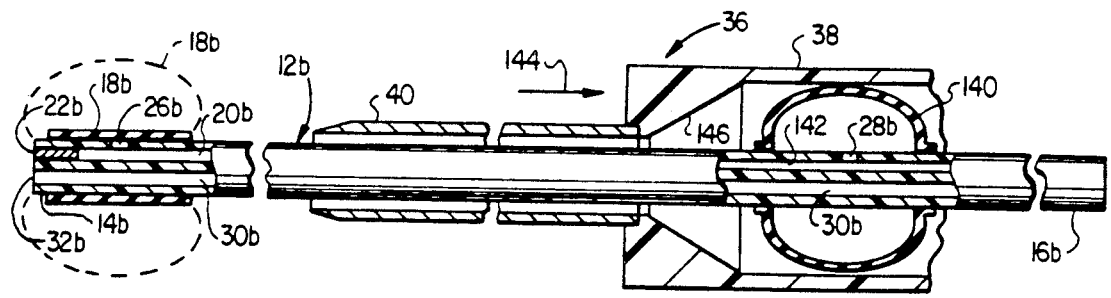
FIGS. 9, 9A, 9B are enlarged scale, longitudinally foreshortened, partially elevational and partially sectioned views of an alternate, dual balloon embodiment of the catheter apparatus and sequentially illustrate its use.
Figure 9A:
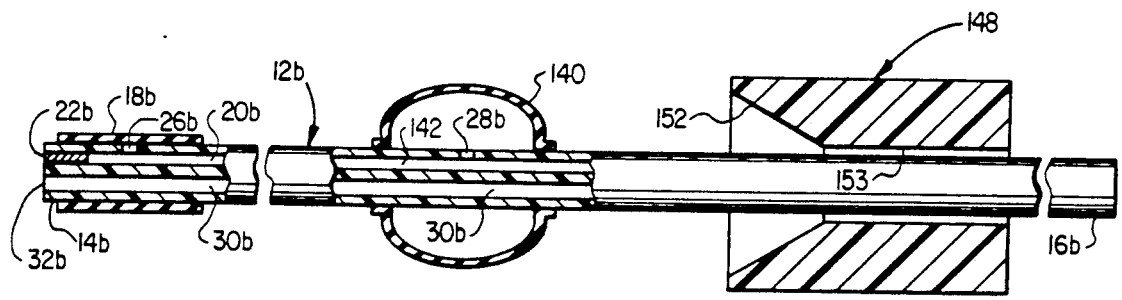
Figure 9B:
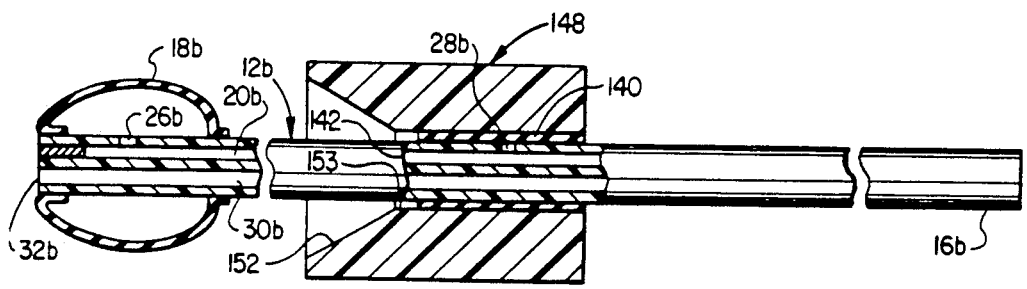

Illustrated in FIGS. 9, 9A and 9B is a second alternate embodiment 12b of the catheter member 12. For ease in comparison, the components of the catheter member 12b similar to those in the catheter member 12 are given identical reference numerals having the subscript "b". The catheter member 12b is utilized in a manner similar to that previously described in conjunction with FIGS. 4-4B but, compared to the catheter member 12, is structurally modified in the following three manners. First, the inlet opening 28b of the inflation lumen 20b is shifted leftwardly away from the proximal catheter member end portion 16b. Secondly, a second inflatable balloon element 140 is secured to and laterally circumscribes the catheter member 12b around the lumen inlet opening 28b. Third, the inflation lumen 20b (which is plugged at its right end) is filled with a pressurized fluid 142. The wall of the balloon 140 is substantially thinner, or is made of a more easily distensible material, than that of the retention balloon 18b, and the pressure of the fluid 142 is sufficiently high such that it normally holds the balloon 140 in an inflated condition while the balloon 18b normally remains in its solid line, fully deflated condition. As will be seen, the added balloon 140 provides the catheter member 12b with a self-inflation feature.

The distal end portion 14b of the modified catheter member 12b is inserted, as previously described, through the hub 38 of the needle 36, and its associated needle member 40, into the epidural space 90 (FIG. 4). The needle 36 is then removed rightwardly from the catheter member 12b as indicated by the arrow 144 in FIG. 9. As the hub 38 is drawn over the inflated balloon 140, a conically sloped interior surface 146 of the hub engages and compresses the balloon 140, and permits its passage through the needle member 40. This compression of the balloon 140 temporarily inflates the retention balloon 18b until the compressed balloon 140 exits the needle member 40, at which time the balloon 140 re-inflates, causing the retention balloon 18b to deflate again. After the needle 36 is pulled off the catheter member 12b, past its proximal end portion 16b, the needle 36 is simply discarded, and a suitable fluid injection device is operatively connected to the proximal inlet opening of the fluid injection lumen 30b to flow an anesthetic fluid leftwardly through the lumen 30b into the epidural space.

Figure 10:
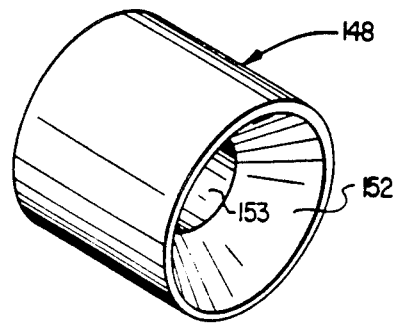
FIG. 10 is a perspective view of a balloon clamp fitting portion of the catheter apparatus shown in FIGS. 9A & 9B.

After the needle 36 has been removed from the catheter member 12b a plastic clamp fitting 148 (FIGS. 9A, 9B and 10) is utilized to compress the balloon 140 to thereby hold the retention balloon 18b in an inflated condition. As best illustrated in FIG. 10, the clamp fitting 148 has a hollow, annular configuration, and is provided at one end with a conically tapered interior end surface 152.

To use the clamp fitting 148, it is threaded, conical end first, onto the proximal catheter end 16b after needle 36 has been removed therefrom. The clamp fitting is then moved leftwardly along the catheter member until the sloped interior surface 152 compresses the balloon 140 and the compressed balloon 140 is moved into the smaller diameter interior portion 153 of the clamp member as illustrated in FIG. 9B. With the balloon 140 held in a deflated condition in this manner, the retention balloon 18b is held in an inflated state within the epidural space. The clamp fitting 148 is then secured to the catheter in a suitable manner, such as by taping. To deflate the retention balloon 18b the clamp member 148 is simply returned to its position depicted in FIG. 9A to allow the pressurized fluid 142 to reinflate the balloon 140 and permit complete deflation of the retention balloon 18b.

As can be seen from the foregoing, the use of the distal tip retention balloon on the various epidural catheter elements representatively described above provides a variety of reliability and safety advantages over conventional catheter apparatus previously used in epidural applications. For example, when inflated in the epidural space, the retention balloon inhibits outward dislodgement of the catheter from the epidural space, and also beneficially inhibits migration of the catheter within the epidural space into, for example, blood vessels, the subarachnoid space, or out a nerve root sleeve. This improved fixation of the catheter within the epidural space also provides for improved post-operative ambulatory analgesia applications in which the catheter is left in place and an analgesic fluid is flowed therethrough into the epidural space.

Additionally, due to the use of the distal end retention balloon, only a very small tip portion of the catheter needs to be initially inserted into the epidural space. This feature, of course, greatly lessens the risk of perforating a blood vessel, or the meninges, upon balloon inflation, and also reduces the potential for creating a unilateral block.

Moreover, the use of dual lumens in the illustrated catheters gives them additional rigidity which facilitates their initial passage through the insertion needle and inhibits undesirable kinking of the catheter. And, of course, even if catheter kinking does occur, the illustrated internal lumen ribs function to essentially prevent a complete fluid flow shut off within the catheter.

As previously described, the catheter elements representatively illustrated herein are configured to be longitudinally passed entirely through an epidural space insertion needle member. This advantageously permits the needle member to be removed from the catheter element before the inlet fitting is secured to the proximal catheter end.

It will be appreciated that a very convenient epidural kit may be provided by appropriately packaging an insertion needle, one of the illustrated catheter elements, and an associated inlet fitting. When the dual balloon catheter element is selected, the kit could also include the clamp fitting illustrated in FIG. 10.

The foregoing detailed description is to be clearly understood as being given by way of illustration and example only, the spirit and scope of the present invention being limited solely by the appended claims.

What is claimed is:

1. For use in conjunction with a hollow needle member insertable through a body portion of a patient into the epidural space, epidural catheter apparatus comprising:

an elongated catheter structure laterally sized to be longitudinally passed entirely through the hollow needle member and including:

an elongated flexible catheter body having distal and proximal end portions, an inflatable balloon element secured to and laterally circumscribing said distal end portion, first lumen means extending longitudinally through said catheter body for flowing a pressurized first fluid from a source thereof into said balloon element to inflate it after said distal end portion has been passed through the inserted needle member into the epidural space, said first lumen means having an inlet opening extending outwardly through said proximal end portion of said catheter body, and second lumen means extending longitudinally through said catheter body for flowing a second fluid from a source thereof into the epidural space through said catheter body distal end portion positioned therein, said second lumen means having an inlet opening extending outwardly through said proximal end portion of said catheter body; and inlet fitting means, removably securable over said proximal end portion of said catheter body with a selectively variable frictional retention force after the inserted needle member has been withdrawn and pulled longitudinally off said catheter body, past its proximal end portion, while said distal end portion remains in the epidural space, for defining separated outward extensions of said first and second lumen means inlet openings through which the first and second fluids may be operatively flowed into and through said first and second lumen means, said inlet fitting means including:

a hollow, generally tubular body having an end opening formed therein, and first and second inlet openings formed therethrough, first and second hollow tubular resilient compression members coaxially disposed within said inlet fitting means body, rigid spacing means positioned between said compression members within the interior of said inlet fitting means body, said proximal end portion of said catheter body being sequentially insertable through said end opening, said first compression member, said spacing means and said second compression member, and cap means tightenable onto said inlet fitting means body to frictionally lock said compression members to said inlet fitting means body and to the inserted proximal end portion of said catheter body, said inlet openings of said first and second lumen means in the frictionally locked proximal end portion of said catheter body being sealingly separated within the interior of said inlet fitting means body, by said compression members, from said end opening and from one another, and respectively communicating with said first and second inlet openings in said inlet fitting means body, said inlet fitting means body having an inlet extension portion circumscribing said first inlet opening of said inlet fitting means body and having an open, threaded outer end, and said epidural catheter apparatus further comprising plunger cap means threadable onto said outer end and operative for pressurizing said first lumen means and inflating said balloon element.

* * * * *